(12) United States Patent
Ito et al.

(10) Patent No.: US 6,264,967 B1
(45) Date of Patent: Jul. 24, 2001

(54) **METHOD FOR ELIMINATING *STAPHYLOCOCCUS AUREUS*, NOVEL MICROORGANISM OF GENUS BRACHYBACTERIUM, AND CARE GARMENT, CARE SHEET OR CARE BEDCLOTHES, EACH BEING IMMOBILIZED WITH MICROORGANISM OF GENUS BRACHYBACTERIUM**

(75) Inventors: Eizo Ito; Naoki Ito, both of Tokyo (JP)

(73) Assignee: Shinei Fermentec Corporation (JP)

( * ) Notice: Subject to any disclaimer, the term of this patent is extended or adjusted under 35 U.S.C. 154(b) by 0 days.

(21) Appl. No.: 09/440,185

(22) Filed: Nov. 15, 1999

(30) Foreign Application Priority Data

Jul. 14, 1999 (JP) .................................. 11-201040
Jul. 27, 1999 (JP) .................................. 11-212609
Jul. 27, 1999 (JP) .................................. 11-212633

(51) Int. Cl.[7] .......................... A01N 25/34; A01N 63/00; C12N 1/20
(52) U.S. Cl. .......................... 424/404; 424/402; 424/780; 424/93.3; 424/93.4; 435/252.1; 435/252.4; 435/882; 435/883
(58) Field of Search .............. 435/252.1, 525.4, 435/882, 883; 424/404, 93.3, 93.4, 402, 780

(56) References Cited

PUBLICATIONS

Takeuchi et al. International Journal of Systematic Bacteriology, vol. 45, No. 1, pp. 160–168, 1995.*

* cited by examiner

*Primary Examiner*—Francisco Prats
*Assistant Examiner*—Susan D. Coe
(74) *Attorney, Agent, or Firm*—Renner, Kenner, Greive, Bobak, Taylor & Weber (57) ABSTRACT

A method for eliminating *Staphylococcus aureus* is disclosed, including inoculating a microorganism of the genus Brachybacterium to *Staphylococcus aureus* to eliminate *Staphylococcus aureus*. A care garment, a care sheet or care bedclothes, each being immobilized with a microorganism or genus Brachybacterium, is also disclosed. One of the microorganismns of the genus Brachybacterium useful in the invention is novel and is deposited as a bacterial strain AAA-a of the genus Brachybacterium (Accession No. FERM BP-6848) in the International Depositary Authority for the deposit of microorganism.

20 Claims, 3 Drawing Sheets

FIG. 1

Bacterial strain AAA-a of genus *Brachybacterium* cultured at 30°C for 4 hours     (×2000)

FIG. 2

Bacterial strain AAA-a of genus *Brachybacterium* cultured at 30°C for 24 hours (×2000)

FIG. 3

METHOD FOR ELIMINATING *STAPHYLOCOCCUS AUREUS*, NOVEL MICROORGANISM OF GENUS BRACHYBACTERIUM, AND CARE GARMENT, CARE SHEET OR CARE BEDCLOTHES, EACH BEING IMMOBILIZED WITH MICROORGANISM OF GENUS BRACHYBACTERIUM

BACKGROUND OF THE INVENTION

1. Field of the Invention

The present invention relates to a method for eliminating *Staphylococcus aureus*, a novel microorganism of the genus Brachybacterium, and a care garment, a care sheet or care bedclothes, each being immobilized with a microorganism of genus Brachybacterium.

2. Description of the Related Art

The following bacteria of the genus Brachybacterium are currently known.

*Brachybacterium conglomeratum*
*Brachybacterium faecium*
*Brachybacterium nesterenkovii*
*Brachybacterium paraconglomeratum*
*Brachybacterium rhamnosum*

However, absolutely no investigation has been done about the industrial applicability of these bacteria of the genus Brachybacterium.

SUMMARY OF THE INVENTION

Therefore, the inventors of the present invention made investigations about the genus Brachybacterium. As a result, it has been found that Branchybacteriau species have an anti-microbial activity against *Staphyrlococcus aureus*.

Based on this finding, it is a first object of the invention to provide a method for eliminating *Staphylococcus aureus* by using Brachybacteriun species.

Further, the inventors made additional investigations to find a novel useful bacterial strain belonging to the genus Brachybacterium. The inventors have successfully separated a bacterial strain with an anti-bacterial function against *Staphylococcus aureus*, like other bacteria of the genus Brachybacteriumn.

Therefore, it is a second object of the invention to provide a novel microorganism of the genus Brachybacterium.

It is a third object of the invention to provide a care garment, a care sheet or care bedclothes, each being immobilized with a microorganism of the genus Brachybacterium.

DETAILED DESCRIPTION OF THE INVENTION

The above objects can be attained by the following constructions (1) and (3).
(1) A method for eliminating *Staphylococcus aureus*, comprising inoculating a microorganism of the genus Brachybacterium to *Staphylococcus aureus* to eliminate *Staphylococcus aureus*.

(2) Anovel microorganism with the following bacteriological profiles, the microorganism belonging to the genus Brachybacterium:
1. Morphology: Polymorphic bacillus (see FIGS. 1 and 2)
2. Gram staining: +
3. Spore: –
4. Mobility: –
5. Oxygen behavior: Aerobic
6. Oxidase: –
7. Catalase: +
8. Color of colony: Yellowish
9. Acid fastness: –
10. Rod-coccus cycle: + (See FIGS. 1 and 2)
11. Elongation of peripheral cells around colony: –
12. Diamino acid in cell wall: Meso-diaminopimelic acid (estimated on the basis of acid hydrolysates from all cells)
13. Glycolyl test: – (Acetyl type)
14. Arabinogalactan polymer in cell wall: – (Estimated on the basis of acid hydrolysates from all cells) – (Estimated on the basis of
15. Mycolic acid: –
16. Quinone series: MK-7, MK-8
17. GC content in bacterial DNA (determined by HPLC): 72 mol %
18. Reduction of nitrate: +
19. Denitrogen reaction: +
20. Methyl red test: –
21. V-P Reaction: –
22. Indole generation: –
23. Hydrogen sulfide generation:
    In TSI agar: –
    In lead acetate agar: – (Lead acetate test paper was suspended for the test, with no addition of lead acetate)
24. Starch hydrolysis: +
25. Utilization of citrate:
    In Koser's culture medium: –
    In Christensen's culture medium: –
26. Utilization of inorganic nitrogen source:
    For nitrate salt –
    For ammonium salt Slight
27. Formation of dye + (Yellowish)
28. Urease –
29. Oxidase –
30. Range of growth (bouillon broth was used for test):
    pH (at an interval of From 6.0 to 10.0 0.5)
    Temperature (at an From 9 to 42° C. interval of 1° C.)
31. Formation of acid:
    D-Abinose: –
    L-Aabinose: +
    D-Xylose: +
    D-Glucose: +
    D-Mannose: +
    D-Fructose: +
    D-Galactose: +
    Maltose: +
    Sucrose: +
    Lactose: +
    Trehalose: +
    D-Sorbitol: –
    D-Mannitol: +
    Inositol: –
    Glycerin: +
    Starch: +

Melezitose: −
D-Ribose: −
32. Formation of gas:
　L-Aabinose: −
　D-Xylose: −
　D-Glucose: −
　D-Mannose: −
　D-Fructose: −
　D-Galactose: −
　Maltose: −
　Sucrose: −
　Lactose: −
　Trehalose: −
　D-Sorbitol: −
　D-Mannitol: −
　Inositol: −
　Glycerin: −
　Starch: −

(3) A care garment, a care sheet and or bedclothes, each being cimmobilized with a microorganism of the genus Brachybacterium.

The tests of the bacteriological properties of the novel Brachybacterium species and their classification were carried out according to the descriptions of the following references.

(1) *International Journal Systematic Bacteriology*, Vol. 38, pp. 45–48 (1988).
(2) *International Journal Systematic Bacteriology*, Vol. 42, pp. 74–78 (1992).
(3) *International Journal Systematic Bacteriology*, Vol. 46, pp. 81–87 (1996).
(4) *International Journal Systematic Bacteriology*, Vol. 45, pp. 160–168 (1995).

Consequently, the microorganism is identified as a Brachybacterium species because the microorganism is a Gram-positive bacillus showing a polymorph with no spore; but the results of the analysis of the bacterial components did not agree with any of the bacterial species described in the references. Thus, the microorganism is confirmed as a novel bacterium belonging to the genus Brachybacterium. The bacterium is deposited as a bacterial strain AAA-a of the genus Brachybacterium (Accession No. FERM BP-6848) at the Microorganism Depository Center, the Life Engineering and Industrial Technology Research Institute, the Agency of Industrial Science and Technology.

1. Morphology: Polymorphic bacillus (see FIGS. 1 and 2)
2. Gram staining: +
3. Spore: −
4. Mobility: −
5. Oxygen behavior: Aerobic
6. Oxidase: −
7. Catalase: +
8. Color of colony: Yellowish
9. Acid fastness: −
10. Rod-coccus cycle: + (See FIGS. 1 and 2)
11. Elongation of peripheral cells around colony: −
12. Diamino acid in cell wall: Meso-diaminopimelic acid (estimated on the basis of acid hydrolysates from all cells)
13. Glycolyl test: − (Acetyl type)
14. Arabinogalactan polymer − (Estimated on the basis of in cell wall: − (Estimated on the basis of acid hydrolysates from all cells)
15. Mycolic acid: −
16. Quinone series: MK-7, MK-8
17. GC content in bacterial DNA (determined by HPLC): 72 mol %
18. Reduction of nitrate: +
19. Denitrogen reaction: +
20. Methyl red test: −
21. V-P Reaction: −
22. Indole generation: −
23. Hydrogen sulfide generation:
　In TSI agar: −
　In leadacetate agar: − (Lead acetate test paper was suspended for the test, with no addition of lead acetate)
24. Starch hydrolysis: +
25. Utilization of citrate:
　In Koser's culture medium: −
　In Christensen's −
　culture medium:
26. Utilization of inorganic nitrogen source:
　For nitrate salt −
　For ammonium salt Slight
27. Formation of dye + (Yellowish)
28. Urease −
29. Oxidase −
30. Range of growth (bouillon broth was used for test):
　pH (at an interval of From 6.0 to 10.0 0.5)
　Temperature (at an From 9 to 42° C. interval of 1° C.)
31. Formation of acid:
　D-Abinose: −
　L-Aabinose: +
　D-Xylose: +
　D-Glucose: +
　D-Mannose: +
　D-Fructose: +
　D-Galactose: +
　Maltose: +
　Sucrose: +
　Lactose: +
　Trehalose: +
　D-Sorbitol: −
　D-Mannitol: +
　Inositol: −
　Glycerin: +
　Starch: +
　Melezitose: −
　D-Ribose: −
32. Formation of gas:
　L-Aabinose: −
　D-Xylose: −
　D-Glucose: −
　D-Mannose: −
　D-Fructose: −
　D-Galactose: −
　Maltose: −
　Sucrose: −
　Lactose: −
　Trehalose: −
　D-Sorbitol: −
　D-Mannitol: −
　Inositol: −

Glycerin: –
Starch: –

The bacterial properties of the novel microorganism of the genus Brachybacterium are described below.

The novel microorganism of the invention can grow well in any of general nutrient culture media.

The microorganism is cultured preferably at about 5 to 30° C., and most preferably at about 18 to 27° C., so that the microorganism grows very well.

The morphological properties of the novel microorganism of the invention are as follows.

(1) Cell morphology and size:

1-1. Culturing in bouillon agar culture medium:

Short bacillus, polymorphic, of a size of 1.2 to 1.4×1.5 to 1.9 microns, when the bacterium is cultured at 30° C. for 6 hours; and Coccobacillus of a size of 1.2 to 1.4×1.2 to 1.5 microns, when the bacterium is cultured at 30° C. for 24 hours.

1-2. Culturing in bouillon liquid culture medium:

Coccobacillus of a size of 1.0 to 1.2×1.3 to 1.4 microns, when the bacterium is cultured at 30° C. for 24 hours.

(2) Polymorphic cell property

Figure 1:
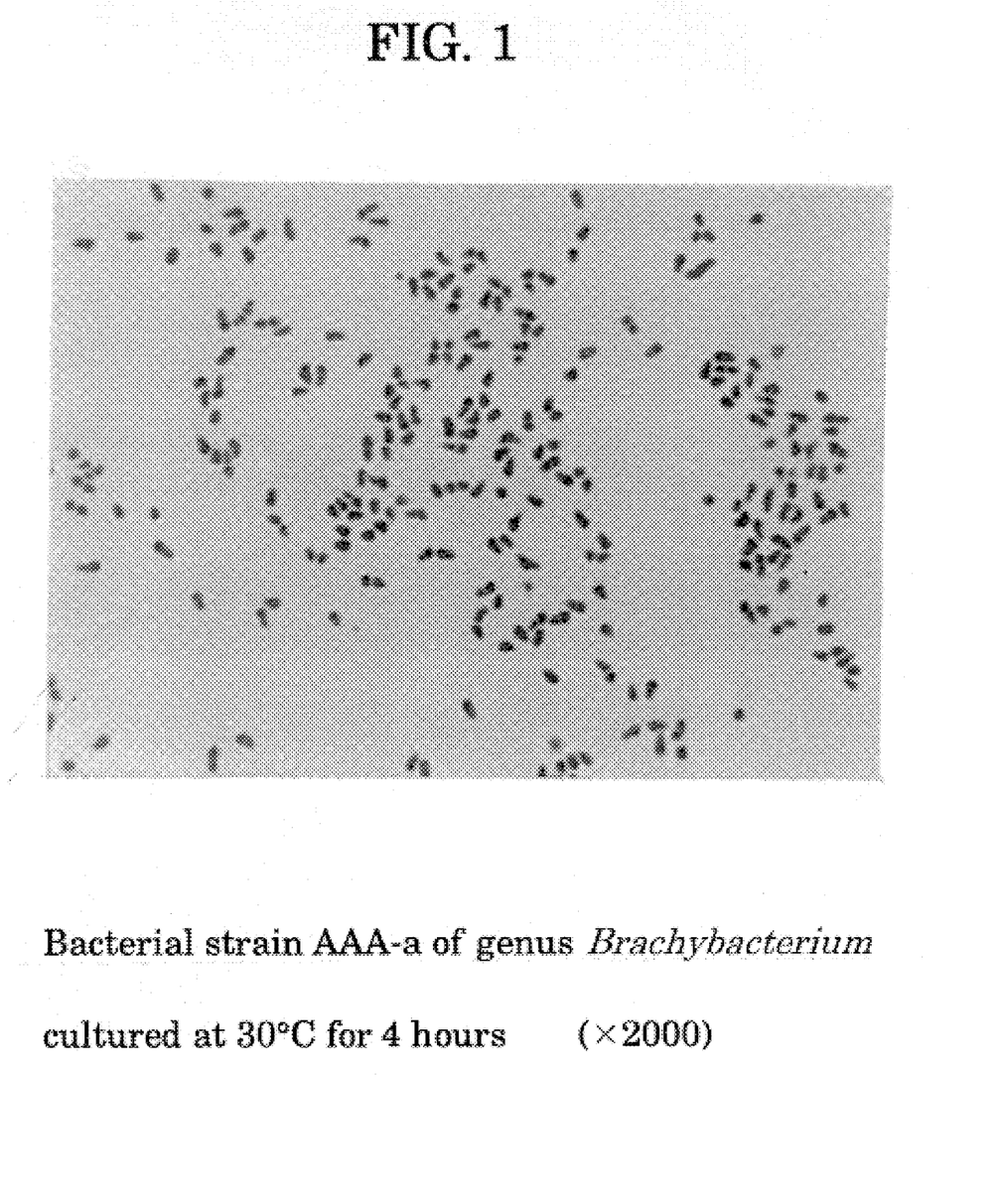
FIG. 1 is a figure representing a microscopic photograph of the morphology of a novel microorganism of the invention 4 hours after cultivation.
Figure 2:
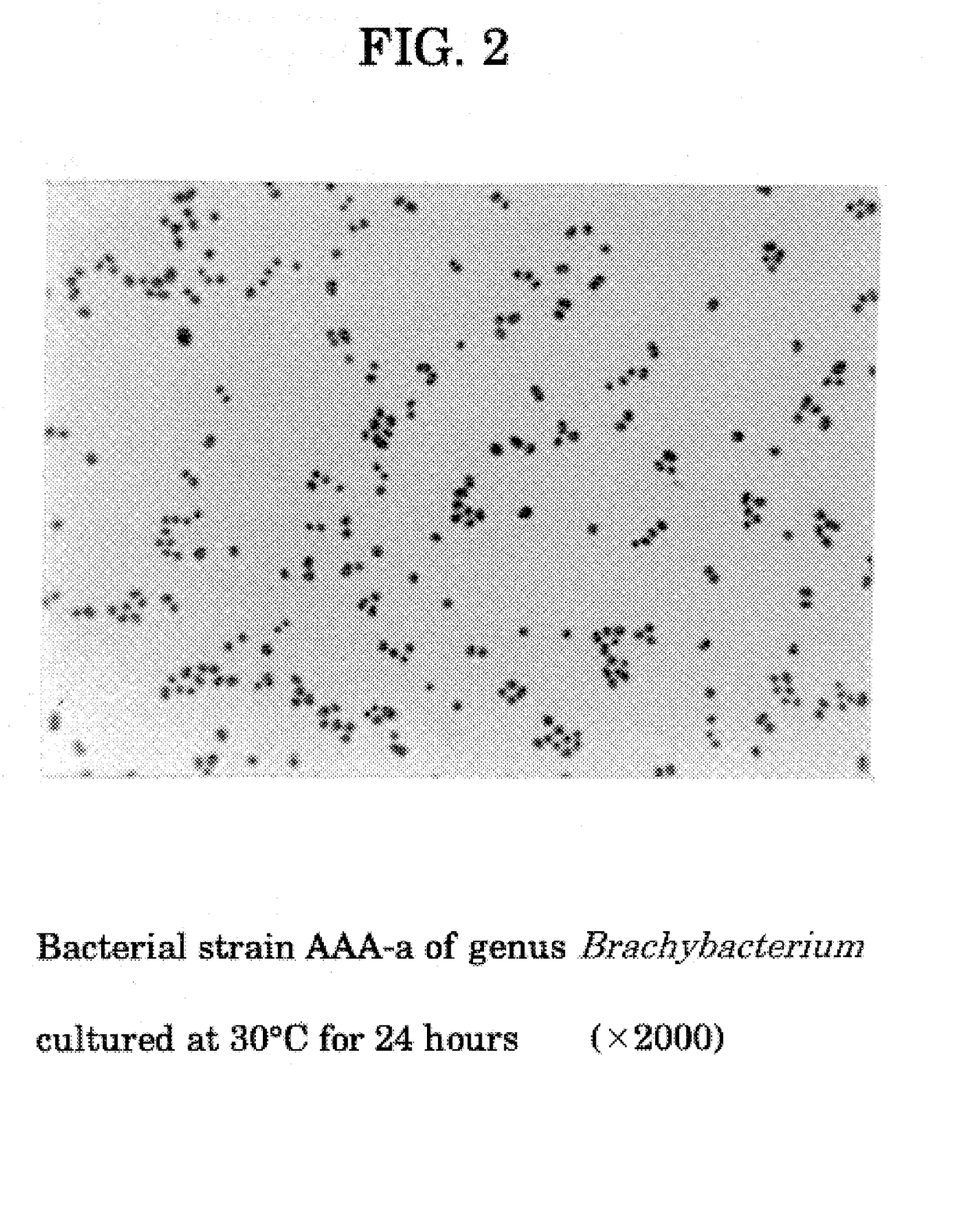
FIG. 2 is a figure representing a microscopic photograph of the morphology of a novel microorganism of the invention 24 hours after cultivation.

Polymorphic property with rod-coccus cycle under observation (see FIGS. 1 and 2).

(3) No mobility found.

(4) No spore formation observed.

The properties of the novel microorganism according to the invention under culture in individual culture media are as follows.

(1) Culturing in Bouillon Agar Plate Culture Medium:

Smooth and glossy colonies with periphery under observation.

Yellowish colony dyes generated under observation.

(2) Culturing in Bouillon Liquid Culture Medium:

Growing bacteria with precipitates in the overall culture medium under observation.

No surface film generated under observation.

(3) Culturing by Using Bouillon Gelatin Puncture:

Bacterial growth in the upper culture medium, but no liquefaction observed.

(4) Culturing in Litmus Milk:

Growing bacteria observed in the overall culture medium, with no solidification or liquefaction observed.

The formation of acid was observed in a slight degree.

The novel microorganism according to the invention dispersed in water or liquid culture media can be used in dispersion states for various uses, but preferably, the novel microorganism is used in the form of a carrier-immobilized microorganism group prepared by immobilizing a group of the microorganism on a carrier for easy handling.

Preferably, the carrier for immobilizing a group of the microorganism thereon has a larger retention volume of the microorganism and readily promotes the activation of the microorganism.

As the carrier, preferably, use is made of rocks (for example, pearlite and diatomaceous earth) or ground rocks, pebble, sand, plastics, ceramics (for example, alumina, silica, natural zeolite, and synthetic zeolite), or talc; specifically, use is preferably made of porous materials with continuous air pores, such as porous ceramics and porous plastics. Preference is given for example to a microfine powder (Pearlite as a trade name) capable of exerting a property to grow bacteria, which is prepared by keeping ground pearlite at a high temperature and a high pressure to thermally treat the pearlite and subsequently reducing the pressure rapidly. Preferably, the pore size of such porous materials is about 2 to 10 $\mu$m. The form of such carrier (form) is any of mass, granule, powder, fine powder, plate material or needle-like material, but preferably, the form is a powdery granule of an average particle size of 2 mm or less, and particularly about 50 $\mu$m to 1 mm. If necessary, such carrier-immobilized microorganism group may satisfactorily be placed in a container with good water permeability or air permeability, including cloths or nets.

As the carrier, use may be made of a woven fabric or non-woven fabric in the form of ribbon or sheet, satisfactorily.

The Brachybacterium species including the novel microorganism can be immobilized on a garment made of a cloth or paper. The cloth-made garment is made of a woven fabric or non-woven fabric (sometimes referred to as carrier hereinafter). The material includes natural fibers such as cotton and linen or synthetic fibers such as nylon, polypropylene or polyester; a cloth made of a woven fabric or non-woven fabric or paper is used as the base material. As described above, the Brachybacterium species is immobilized on the cloth. The Brachybacterium species is partially immobilized thereon; otherwise, ribbons made of the Brachybacterium species-immobilized cloth or paper are structurally stitched or attached on a garment.

As a partial material of the cloth composing the garment, a fiber preferably mixed internally with an oxide ceramics particle with a far infrared light-emitting property is used. For use herein, the infrared light-emitting oxide ceramics includes a clay sintered after addition of M metal oxides such as titanium oxide, zirconium oxide and tin oxide; the oxide ceramics specifically includes $ZrO_2$—$SiO_2$—based ceramics, $Al_2O_3$—$SiO_2$—based ceramics, $TiO_2$—$Cr_2O_3$-based ceramics, $Al_2O_3$—(Si, Ti $C_2$-based ceramics, and (Al, Fe, B, Cr)$_2$O$_3$—$SiO_2$-(alkali metal or alkaline earth metal) oxide-based ceramics.

Herein, the oxide ceramics has a far infrared light-emitting property emitting an electromagnetic wave whose wavelength peak is 8 to 14 $\mu$m corresponding to the infrared light absorption wavelength in humans, when the oxide ceramics is heated at 35.5 to 36.5° C. substantially equal to the human body temperature.

Also, the Brachybacterium species including the novel microorganism may be immobilized on a sheet made of a cloth or paper. As the sheet made of a cloth, use is made of a woven fabric or non-woven fabric (sometimes referred to as carrier hereinbelow, too).

So as to immobilize a group of the microorganism on such carrier, a dispersion of a group of the microorganism according to the invention (sometimes abbreviated as microorganism group hereinafter) is mixed with the carrier, and the resulting mixture is dried; otherwise, the microorganism group is satisfactorily cultured directly in the carrier.

The amount of the microorganism group immobilized on the carrier differs, depending on the conditions for immobilization, but the amount is preferably from 5 cells to 200 hundred million cells/cm$^3$, and more preferably from 10 bodies to 100 hundred million cells/cm$^3$.

The carrier-immobilized microorganism group of the invention effectively exerts an anti-bacterial activity against *Staphylococcus aureus* to eliminate the bacterium. Furthermore, it is verified that the novel microorganism of the invention exhibits a deodorizing effect when used in pig farms and public lavatories.

The Brachybacterium species-immobilized garment or sheet of the invention undoubtedly exerts an effect of preventing bedsore from patients under long-term treatment. Furthermore, the deodorizing effect has also been confirmed.

Further, the novel microorganism has been confirmed to be safe at oral dosing tests in mice. The above effect demonstrates that the Brachybacterium species-immobilized garment or sheet can be used as a care garment or a care sheet. The care sheet can be used as it is or as a sheet with ornaments attached thereon. The sheet is also used in bedclothes, where the sheet is filled inside.

Figure 3:
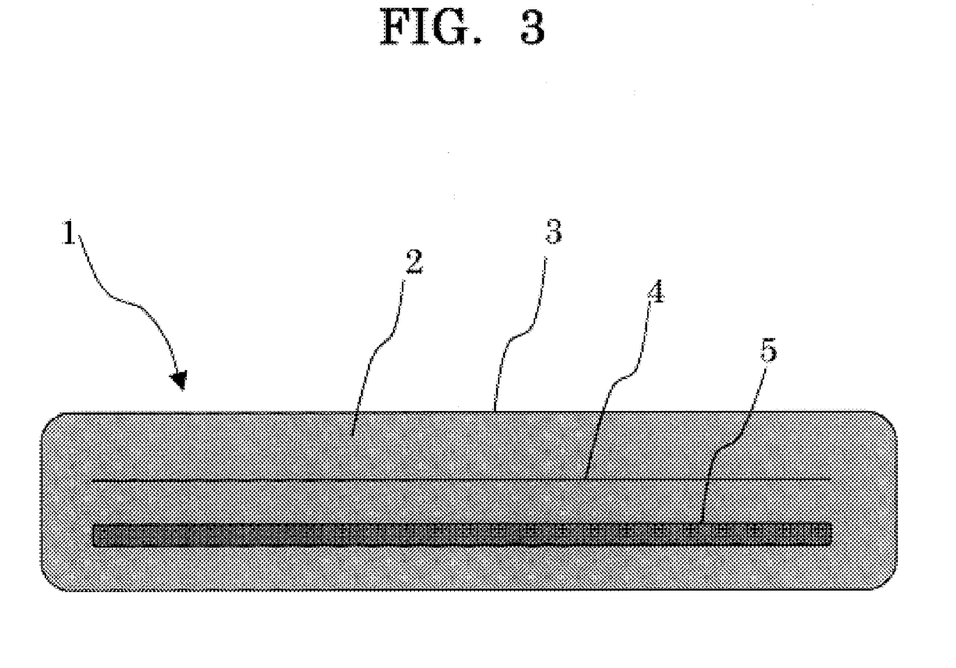
FIG. 3 is a cross-sectional view of a type of a bedcloth in a preferable embodiment of the invention.

The invention will now be described in a preferable bedclothes embodiment in detail. In the following description, a thick bedspread is illustrated but the invention is not limited to the embodiment. FIG. 3 depicts a cross-sectional view of a thick bedspread 1 in a preferred embodiment of the invention. The thick bedspread 1 comprises an inner cotton filling 2 covered with a fabric cover-up 3; in the cotton filling 2, a Brachybacterium species-immobilized sheet 4 is embedded and arranged, preferably together with a far infrared light-emitting substance-immobilized sheet 5; and in the cotton filling 2, both of the sheets 4 and 5 elongate in its entirety.

As the inner cotton filling 2, use can preferably be made of general cotton, wool, floss silk, camel, or chemical fibers such as polyester or rayon.

The fabric cover-up 3 is preferably made of a general cloth prepared by using cotton, wool, silk or synthetic fibers such as polyester or rayon.

The Brachybacterium species-immobilized sheet 4 essentially comprises natural fibers such as cotton and linen and synthetic fibers such as nylon, polypropylene and polyester to prepare a cloth or sheet in the form of a woven fabric or non-woven fabric, or comprises paper. The Brachybacterium species is immobilized on the cloth as described above.

The far infrared light-emitting substance-immobilized sheet 5 comprises a synthetic fiber such as polyester or rayon, where oxide ceramics particles with a far infrared light-emitting property are preferably mixed in the fiber. Herein, use is made of the far infrared ray-emitting oxide ceramics prepared by adding M metal oxides such as titanium oxide, zirconium oxide and tin oxide to a clay for sintering, specifically including $ZrO_2$—$SiO_2$-based ceramics, $Al_2O_3$—$SiO_2$-based ceramics, $TiO_2$—$Cr_2O_3$-based ceramics, $Al_2O_3$-(Si, Ti)$C_2$-based ceramics, and (Al, Fe, B, Cr)$_2O_3$—$SiO_2$-(alkali metal or alkaline earth metal) oxide-based ceramics.

Herein, the oxide ceramics has a far infrared light-emitting property emitting electromagnetic wave whose wavelength peak is 8 to 14 μm corresponding to the infrared ray absorption wave length in humans when the oxide ceramics is heated at 35.5 to 36.5° C. substantially equal to the human body temperature.

In the above embodiment, the Brachybacterium species and the far infrared light-emitting substance are independently immobilized on different immobilizing sheets, but they are immobilized on the same one immobilizing sheet. Still furthermore, the Brachybacterium species and the far infrared ray-emitting substance may satisfactorily be deposited directly on the inner cotton filling 2 or on the fabric cover-up 3, with no use of any immobilizing sheet. In accordance with the invention, the fabric cover-up 3 immobilizing thereon the Brachybacterium species and the far infrared ray-emitting substance is also represented by the phrase fabric cover-up 3 comprising the Brachybacterium species and the far infrared ray-emitting substance.

The invention is now described in detail with reference to the following Examples.

EXAMPLE 1

First of all, a culture medium of the following composition was prepared.

Culture medium:

Peptone: 5 g

Meat extract: 5 g

Water: 500 ml pH of culture medium: 6.8±0.2.

A bacterial strain AAA-a of the genus Brachybacterium was inoculated in the culture medium of the above composition, for agitation culture at 30° C. When the bacteria reached a logarithmic phase, the culture medium was diluted with a sterilized physiological saline solution to adjust the viable cell number to about $1\times10^8$ cells/ml; and the adjusted solution was directly poured and inoculated on Staphylococcus aureus. Then, halochromism was observed. The same experiment was done on other Brachybacterium species other than the aforementioned species. In this case, halochromism was also observed against Staphylococcus aureus, although the function was poorer than that observed in the case of the novel bacterial strain.

Separately, the resulting adjusted solution was applied to a centrifuge, to separate the bacteria; then, the bacteria were rinsed well and deposited on a carrier to prepare a powder. As the carrier, use was made of burned and ground diatomaceous earth.

The powdery bacterial strain AAA-a of the genus Brachybacterium was poured on rotten whole sardine, which was then stored at 25° C. Two hours after the storage, the odor was checked. The odor was apparently decreased. When the bacterial strain AAA-a of the genus Brachybacterium was poured on fresh sardine to be kept at 25° C. under storage, no putrefactive odor was smelled even 48 hours later. Separately, sardine stored at 25° C. as it was with no treatment comprising pouring the bacterial strain AAA-a of the genus Brachybacterium, smelled strongly 24 hours later.

As has been described above, the bacterial strain AAA-a of the genus Brachybacterium is endowed with a deodorizing action and an action to retain freshness.

EXAMPLE 2

A bacterial strain AAA-a of the genus Brachybacterium was inoculated on a Hart infusion-bouillon culture medium for agitation culture at 30° C.

When the bacteria reached a logarithmic phase, the culture medium was diluted with a sterilized physiological saline solution, to adjust the viable cell number to about $1\times10^8$ cells/ml. The resulting adjusted solution was coated on a carrier such as a cloth or paper to a final concentration of about $1\times10^4$ cells/cm$^2$. The thus prepared material was dried and used to prepare a bath robe.

A patient absolutely unable to leave bed wore the bath robe. Even 6 months later, no bedsore occurred.

In patients in the same circumstance except for no use of the bath robe, bedsore occurred at an early stage of one month later to a late stage of 3 months later. In any of these patients, no specific device was used for preventing bedsore.

With nutrients such as sweat, the bacteria grew to $3\times10^7$ cells/cm$^2$, 6 hours later. The halochromism of the growing Brachybacterium species can eliminate Staphylococcus aureus. It is suggested that the halochromism can prevent pneumonia, sepsis, myelitis, staphylococcal enteritis, staphylococcal burn-like syndrome, and toxic shock syndrome, all of which are caused by Staphylococcus.

EXAMPLE 3

A bacterial strain AAA-a of the genus Brachybacterium was inoculated on a Hart infusion-bouillon culture medium for agitation culture at 30° C.

When the bacteria reached a logarithmic phase, the culture medium was diluted with sterilized physiological saline, to adjust the viable cell number to about $1\times10^8$ cells/ml. The resulting adjusted solution was coated on a carrier such as cloth or paper to a final concentration of about $1\times10^4$ cells/cm$^2$. The thus prepared material was dried and used to prepare a sheet of 90×180 cm.

The sheet was used for a patient absolutely unable to leave bed. Even 6 months later, no bedsore occurred. With nutrients such as sweat, six hours later, the bacteria grew to $3\times10^7$ cells/cm$^2$. It is indicated that the halochromism of the growing Brachybacterium species can eliminate *Staphylococcus aureus* or can prevent bedsore on the assumption of the growth of *Staphylococcus aureus*.

In patients in the same circumstance except for no use of the inventive sheet, bedsore occurred as early as one month later to 3 months later at a late stage.

It is suggested that the inventive sheet and the like can prevent pneumonia, sepsis, myelitis, staphylococcal enteritis, staphylococcal burn-like syndrome, and toxic shock syndrome, all of which are caused by Staphylococcus.

What is claimed is:

1. A method for eliminating *Staphylococcus aureus*, comprising inoculating a microorganism of the genus Brachybacterium to *Staphylococcus aureus* to eliminate *Staphylococcus aureus*.

2. A biologically pure culture of a novel microorganism of the genus Brachybacterium, the microorganism having the following bacteriological properties:
   A. Morphology: Polymorphic bacillus
   B. Gram staining: +
   C. Spore: −
   D. Mobility −
   E. Oxygen behavior Aerobic
   F. Oxidase: −
   G. Catalase: +
   H. Acid fastness: −
   I. Rod-coccus cycle: +
   J. Elongation of peripheral cells around colony: −
   K. Diamino acid in cell wall: Meso-diaminopimelic acid
   L. Glycolyl test: −
   M. Arabinogalactan polymer in cell wall: −
   N. Mycolic acid: −
   O. Quinone series: MK-7, MK-8
   P. GC content in bacterial DNA determined by HPLC: 72 mol %
   Q. Reduction of nitrate: +
   R. Denitrogen reaction: +
   S. Methyl red test: −
   T. V-P Reaction: −
   U. Indole generation: −
   V. Hydrogen sulfide generation:
      In TSI agar: −
      In lead acetate agar: −
   W. Starch hydrolysis: +
   X. Utilization of citrate:
      In Koser's culture medium: −
      In Christensen's culture medium: −
   Y. Formation of dye: +
   Z. Urease −
   AA. Range of growth in bouillon broth:
      pH, at an interval of 0.5: From 6.0 to 10.0
      Temperature at an interval of 1° C.: From 9 to 42° C.
   BB. Formation of acid:
      D-Arabinose: −
      L-Arabinose: +
      D-Xylose: +
      D-Glucose: +
      D-Mannose: +
      D-Fructose: +
      D-Galactose: +
      Maltose: +
      Sucrose: +
      Lactose: +
      Trehalose: +
      D-Sorbitol: −
      D-Mannitol: +
      Inositol: −
      Glycerin: +
      Starch: +
      Melezitose: −
      D-Ribose: −
   CC. Formation of gas:
      L-Arabinose: −
      D-Xylose: −
      D-Glucose: −
      D-Mannose: −
      D-Fructose: −
      D-Galactose: −
      Maltose: −
      Sucrose: −
      Lactose: −
      Trehalose: −
      D-Sorbitol: −
      D-Mannitol: −
      Inositol: −
      Glycerin: −
      Starch: −.

3. A garment comprising an immobilized microorganism of the genus Brachybacterium.

4. A garment according to claim 3, wherein the microorganism of the genus Brachybacterium has the following bacteriological properties:
   A. Morphology: Polymorphic bacillus
   B. Gram staining: +
   C. Spore: −
   D. Mobility −
   E. Oxygen behavior Aerobic
   F. Oxidase: −
   G. Catalase: +
   H. Acid fastness: −
   I. Rod-coccus cycle: +
   J. Elongation of peripheral cells around colony: −
   K. Diamino acid in cell wall: Meso-diaminopimelic acid
   L. Glycolyl test: −
   M. Arabinogalactan polymer in cell wall: −
   N. Mycolic acid: −
   O. Quinone series: MK-7, MK-8
   P. GC content in bacterial DNA determined by HPLC: 72 mol %
   Q. Reduction of nitrate: +
   R. Denitrogen reaction: +
   S. Methyl red test: −
   T V-P Reaction: −
   U. Indole generation: −
   V. Hydrogen sulfide generation:
      In TSI agar: −
      In lead acetate agar: −
   W. Starch hydrolysis: +

X. Utilization of citrate:
   In Koser's culture medium: −
   In Christensen's culture medium: −
Y. Formation of dye: +
Z. Urease −
AA. Range of growth in bouillon broth:
   pH, at an interval of 0.5: From 6.0 to 10.0
   Temperature at an interval of 1° C.: From 9 to 42° C.
BB. Formation of acid:
   D-Arabinose: −
   L-Arabinose: +
   D-Xylose: +
   D-Glucose: +
   D-Mannose: +
   D-Fructose: +
   D-Galactose: +
   Maltose: +
   Sucrose: +
   Lactose: +
   Trehalose: +
   D-Sorbitol: −
   D-Mannitol: +
   Inositol: −
   Glycerin: +
   Starch: +
   Melezitose: −
   D-Ribose: −
CC. Formation of gas:
   L-Arabinose: −
   D-Xylose: −
   D-Glucose: −
   D-Mannose: −
   D-Fructose: −
   D-Galactose: −
   Maltose: −
   Sucrose: −
   Lactose: −
   Trehalose: −
   D-Sorbitol: −
   D-Mannitol: −
   Inositol: −
   Glycerin: −
   Starch: −.

5. A garment according to claim 3, which is a garment for sleeping.

6. A garment according to claim 3, which is a pair of gloves.

7. A garment according to claim 3, which is a pair of socks or traditional Japanese-style socks.

8. A garment according to claim 3, which is an underwear.

9. A sheet comprising an immobilized microorganism of the genus Brachybacterium.

10. A sheet according to claim 9, wherein the microorganism of the genus Brachybacterium has the following bacteriological properties:
   A. Morphology: Polymorphic bacillus
   B. Gramstaining: +
   C. Spore: −
   D. Mobility −
   E. Oxygen behavior Aerobic
   F. Oxidase: −
   G. Catalase: +
   H. Acid fastness: −
   I. Rod-coccus cycle: +
   J. Elongation of peripheral cells around colony: −
   K. Diamino acid in cell wall: Meso-diaminopimelic acid
   L. Glycolyl test: −
   M. Arabinogalactan polymer in cell wall: −
   N. Mycolic acid: −
   O. Quinone series: MK-7, MK-8
   P. GC content in bacterial DNA determined by HPLC: 72 mol %
   Q. Reduction of nitrate: +
   R. Denitrogen reaction: +
   S. Methyl red test: −
   T V-P Reaction: −
   U. Indole generation: −
   V. Hydrogen sulfide generation:
      In TSI agar: −
      In lead acetate agar: −
   W. Starch hydrolysis: +
   X. Utilization of citrate:
      In Koser's culture medium: −
      In Christensen's culture medium: −
   Y. Formation of dye: +
   Z. Urease −
   AA. Range of growth in bouillon broth:
      pH, at an interval of 0.5: From 6.0 to 10.0
      Temperature at an interval of 1° C.: From 9 to 42° C.
   BB. Formation of acid:
      D-Arabinose: −
      L-Arabinose: +
      D-Xylose: +
      D-Glucose: +
      D-Mannose: +
      D-Fructose: +
      D-Galactose: +
      Maltose: +
      Sucrose: +
      Lactose: +
      Trehalose: +
      D-Sorbitol: −
      D-Mannitol: +
      Inositol: −
      Glycerin: +
      Starch: +
      Melezitose: −
      D-Ribose: −
   CC. Formation of gas:
      L-Arabinose: −
      D-Xylose: −
      D-Glucose: −
      D-Mannose: −
      D-Fructose: −
      D-Galactose: −
      Maltose: −
      Sucrose: −
      Lactose: −
      Trehalose: −
      D-Sorbitol: −
      D-Mannitol: −
      Inositol: −
      Glycerin: −
      Starch: −.

11. A bedclothes comprising a sheet according to claim 9, which is a bed sheet.

12. A bedclothes comprising a sheet according to claim 9, which is a blanket.

13. A bedclothes according to claim 12, wherein said blanket is a cotton blanket.

14. A bedclothes comprising a sheet according to claim 9, which is a bedquilt.

15. A bedclothes according to claim 14, wherein said bedquilt is a comforter, a top covering or a bedspread.

16. A bed mattress made from a sheet according to claim 9.

17. A pillow made from a sheet according to claim 9.

18. The microorganism of claim 2, wherein said microorganism of the genus Brachybacterium is FERM BP-6848.

19. The garment of claim 4, wherein said microorganism of the genus Brachybacterium is FERM BP-6848.

20. The sheet of claim 9, wherein the microorganism of the genus Brachybacterium is FERM BP-6848.

* * * * *